(12) United States Patent
Salgo et al.

(10) Patent No.: US 8,096,947 B2
(45) Date of Patent: Jan. 17, 2012

(54) QUANTIFICATION AND DISPLAY OF CARDIAC CHAMBER WALL THICKENING

(75) Inventors: Ivan Salgo, Pelham, MA (US); Scott Settlemier, Marlborough, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 498 days.

(21) Appl. No.: 12/301,499

(22) PCT Filed: May 17, 2007

(86) PCT No.: PCT/IB2007/051895
§ 371 (c)(1),
(2), (4) Date: Nov. 19, 2008

(87) PCT Pub. No.: WO2007/138522
PCT Pub. Date: Dec. 6, 2007

(65) Prior Publication Data
US 2009/0131788 A1  May 21, 2009

Related U.S. Application Data

(60) Provisional application No. 60/803,148, filed on May 25, 2006, provisional application No. 60/823,114, filed on Aug. 22, 2006.

(51) Int. Cl.
*A61B 8/00* (2006.01)
(52) U.S. Cl. .................. 600/437; 600/450; 382/128
(58) Field of Classification Search .......... 600/437–465; 382/128–132
See application file for complete search history.

(56) References Cited

U.S. PATENT DOCUMENTS

| | | | |
|---|---|---|---|
| 5,195,521 A | 3/1993 | Melton, Jr. et al. | |
| 5,544,656 A * | 8/1996 | Pitsillides et al. | 600/450 |
| 5,797,396 A | 8/1998 | Geiser et al. | |
| 5,964,754 A * | 10/1999 | Osypka | 606/37 |
| 6,540,699 B1 * | 4/2003 | Smith | 600/587 |
| 6,628,743 B1 * | 9/2003 | Drummond et al. | 378/8 |
| 6,638,221 B2 * | 10/2003 | Abe et al. | 600/437 |
| 7,318,804 B2 * | 1/2008 | Weitzel et al. | 600/438 |

(Continued)

OTHER PUBLICATIONS

Stanley, T.E., et al., "Quantitative Analysis of Transesophageal Echocardiograms for the Intraoperative Setting: Clinical Need and Initial Experience," Images of the Twenty-First Century. Seattle, Nov. 9-12, 1989, Procs. of the Ann. Int'l Conf. of Eng. in Med. and Bio. Soc., New York, IEEE, US, vol. Part 5 Conf. 11, Nov. 9, 1989, pp. 1569-1570, XP000129522.

(Continued)

*Primary Examiner* — Sanjay Cattungal
(74) *Attorney, Agent, or Firm* — W. Brinton Yorks, Jr.

(57) ABSTRACT

An ultrasonic imaging system and method are described for quantification and display of myocardial wall thickening. The endocardial and epicardial borders in an image sequence are defined over a heart cycle and changes in the distance between the borders are tracked at specified locations around the myocardium over the heart cycle, The changes in distance are presented to the user in a graphical format, preferably together with another measure of the cardiac cycle such as chamber volume variation, ejection fraction, or the ECG waveform. The changes in the distance of chord lengths across the myocardium provide a direct indication of wall thickness variation at the specified locations. Preferably the tracking of the specified locations over the heart cycle is done by speckle tracking. The inventive technique can also represent strain at the specified locations of the myocardium.

14 Claims, 6 Drawing Sheets

U.S. PATENT DOCUMENTS

| | | | |
|---|---|---|---|
| 7,356,172 B2* | 4/2008 | Fan et al. | 382/128 |
| 7,422,561 B2* | 9/2008 | Kanai et al. | 600/437 |
| 7,647,109 B2* | 1/2010 | Hastings et al. | 607/32 |
| 7,650,186 B2* | 1/2010 | Hastings et al. | 607/32 |
| 7,708,692 B2* | 5/2010 | Kato et al. | 600/438 |
| 2002/0072671 A1* | 6/2002 | Chenal et al. | 600/450 |
| 2003/0013964 A1* | 1/2003 | Bjaerum et al. | 600/443 |
| 2005/0075567 A1* | 4/2005 | Skyba et al. | 600/443 |
| 2005/0124881 A1* | 6/2005 | Kanai et al. | 600/437 |
| 2006/0004288 A1* | 1/2006 | Kato et al. | 600/443 |
| 2006/0085041 A1* | 4/2006 | Hastings et al. | 607/33 |
| 2006/0085042 A1* | 4/2006 | Hastings et al. | 607/33 |
| 2006/0184190 A1* | 8/2006 | Feiler et al. | 606/185 |
| 2008/0294048 A1* | 11/2008 | Salgo et al. | 600/450 |

OTHER PUBLICATIONS

Marwick, et al., "Mesurement of Strain and Strain Rate by Echocardiography," Journal of the American College of Cardiology, Elsevier, New York, NY, US, vol. 47, No. 7, Apr. 4, 2006, pp. 1313-1327, XP005388723.

\* cited by examiner

QUANTIFICATION AND DISPLAY OF CARDIAC CHAMBER WALL THICKENING

This application claims the benefit of U.S. provisional patent application Ser. Nos. 60/803,148, filed May 25, 2006, and 60/823,114, filed Aug. 22, 2006.

This invention relates to medical diagnostic ultrasound systems and, in particular, to ultrasound systems which perform quantified measurements of echocardiographic images.

There exist many ultrasonic methods to quantify cardiac chamber function. Ventricular wall motion indicative of myocardial infarction and ejection fraction are basic diagnostic tools for echocardiographers. These diagnostic tools require that the heart chamber be defined and tracked over a series of images over the cardiac cycle so that measurements of the delineated myocardium and heart chamber can be made. Techniques for delineating the heart wall in an ultrasound image include for example automated border tracking of blood tissue interfaces and tissue Doppler imaging of cardiac wall motion to quantify velocity of contraction, among others. The ability to delineate and track myocardial motion is also important for diagnosing the synchronicity of the electrical stimulation of the heart, referred to as electromechanical transduction. The heart is commanded to contract by electrochemical signals passed by sodium and potassium channels in the muscle cells of the myocardium. These signals, dispersed as they are over the entire heart muscle, should command the heart muscle cells to contract at the same instant in time. When this happens the heart contracts from a relaxed, full volume to a contracted minimal volume, thereby pumping a maximal volume of blood with each heartbeat. This is a characteristic of a healthy heart. However, when the signals that stimulate this contraction cause different regions of the heart to contract at different times, the erratic contraction will pump less than the maximal volume of blood, producing reduced efficiency and taxing the heart over time. It is desirable to be able to diagnose this condition so that the necessary treatment regime, generally the implantation of a pacemaker with leads placed to force synchronous contractions, can be performed if needed. This diagnosis and its treatment is referred to as cardiac resynchronization therapy, or CRT.

A disease condition which can affect electromechanical transduction of the heart is left bundle branch block. Left bundle branch block occurs when transmission of the cardiac electrical impulse is delayed or fails to conduct along the rapidly conducting fibers of the main left bundle branch or in both left anterior and posterior fascicles. This can cause the left ventricle to depolarize slowly via cell-to-cell conduction spreading from the right ventricle to the left ventricle. This condition results in a loss of synchronicity of chamber contraction and a consequent inefficient ejection of blood volume from the chamber. Accordingly it is desirable to be able to effectively and accurately identify and quantify indications and effects of this condition such as heart wall thickening. Heretofore, wall thickening has been assessed by subjective measurements by experts.

Identifying wall thickening requires delineation of the endocardium and the epicardium. At present, there are no reliable methods to extract epicardial borders by the usual expedient of extracting image gradients. Furthermore, while wall thickening can in theory be assessed by tissue Doppler methods, the Doppler effect is subject to orientation limitations of the acoustic beam, with detected velocities varying in proportion to the relation between the direction of motion and the direction of the interrogating ultrasound beams. For instance, if the myocardium is moving at right angles to the acoustic line (the beam direction), no motion will be detected. Doppler methods can also only indirectly measure thickening. They measure velocities which must be then be integrated, introducing noise and potential error, in order to determine displacements and hence thickening. Thus it is desirable to be able to directly identify and quantify myocardial wall thickening.

In accordance with the principles of the present invention, a region of interest (ROI) in a cardiac ultrasound image is defined with points on the endocardium and the epicardium for a frame at a point in the cardiac cycle. These points are then speckle/texture tracked over the cardiac cycle. The distance between corresponding endo- and epicardial tracked points is calculated for each frame, yielding direct measures for length and Lagrangian strain or other fractional changes in length from initial value. Both measures are direct measurements of wall thickening and are displayed in graphs as a function of time. The inventive technique is not limited to gradient detection methods (blood-tissue interface), is not subject to angular deviations of tissue motion relative to the ultrasound beam characteristic of Doppler measurements, and provides a direct measurement of displacements and hence thickening.

Figure 1:
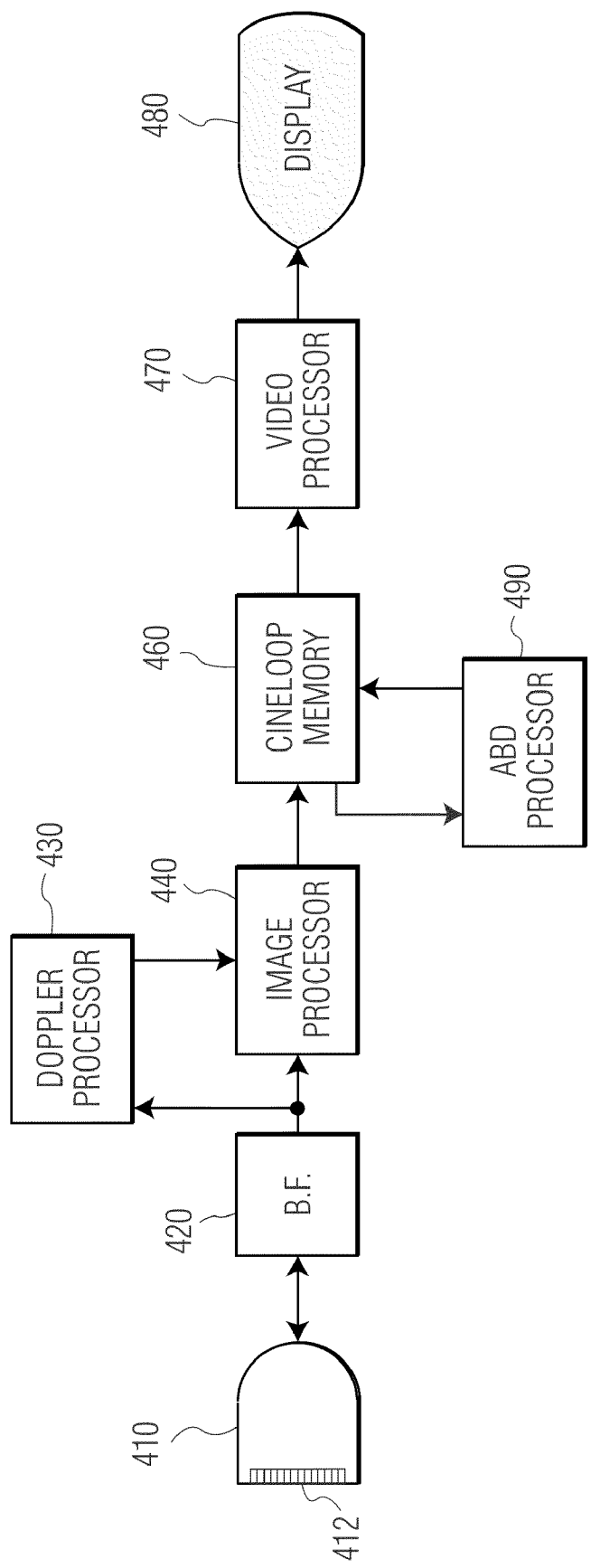
FIG. 1 illustrates in block diagram form an ultrasound system with an automatic border detection processor constructed in accordance with the principles of the present invention.

Referring first to FIG. 1, an ultrasonic diagnostic imaging system constructed in accordance with the principles of the present invention is shown in block diagram form. A probe or scanhead 410 which includes a one dimensional (1D) or two dimensional (2D) array 412 of transducer elements transmits ultrasonic waves and receives ultrasonic echo signals. This transmission and reception is performed under control of a beamformer 420 which processes received echo signals to form coherent beams of echo signals from the anatomy being scanned. The echo information is Doppler processed by a Doppler processor 430 when Doppler information is to be presented, and the processed Doppler information is coupled to an image processor 440 which forms 2D or 3D Doppler images. For B mode imaging of tissue structure the echo signals are image processed by amplitude detection and scan converted into the desired image format for display. The images pass through a Cineloop® memory 460 from which they may be coupled directly to a video processor 470 for display on an image display 480. The Cineloop memory can also be operated to capture a sequence of recently acquired real time images for storage and later inspection and diagnosis. The sequence of captured images, referred to as a "loop" of images, can extend over one or more heart cycles. The images may also be applied to an automatic border detection (ABD) processor 490 which operates on the 2D or 3D images to define anatomical borders and boundaries in the images as described below. The defined borders are graphically overlaid on the images which are coupled to the video processor 470 for display. The system may operate to define and display borders on loops of images saved in the Cineloop memory 460, or to display borders drawn on real time images produced during live scanning of a patient.

Figure 2:
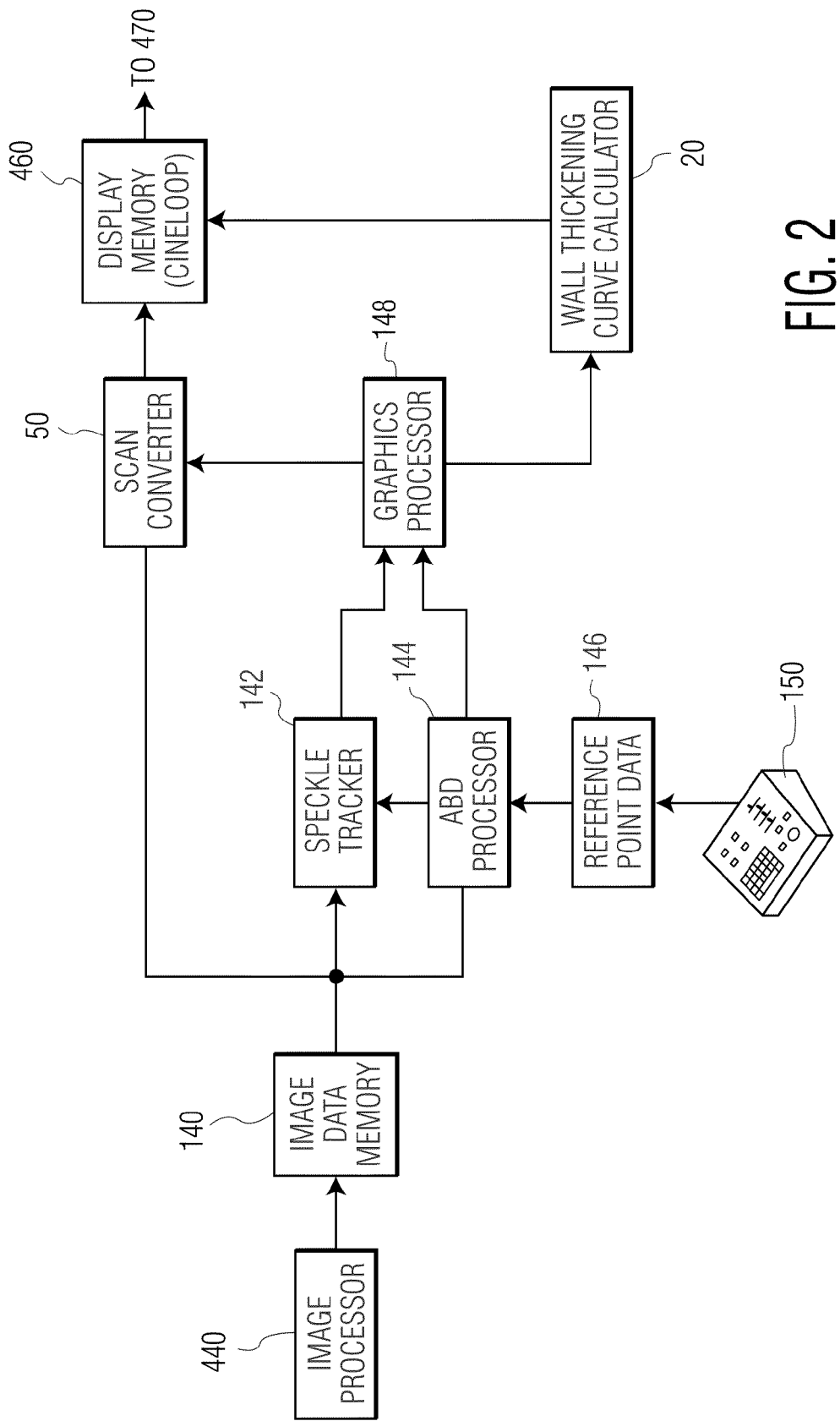
FIG. 2 illustrates a portion of the ultrasound system of FIG. 1 in greater detail.

FIG. 2 is a detailed block diagram of the portion of the ultrasound system between the image processor 440 and the video processor 470 of FIG. 1. The image processor 440 produces scanline data of an image which is stored in image data memory 140. A first, starting point image of a sequence of heart images is analyzed by border detection of a heart chamber by an ABD processor 144 as described more fully below. When the border is defined in this first image its location is tracked through subsequent images by a speckle tracker 142. The initially defined border and the border in subsequent images are drawn by a graphics processor 148. The ultrasound images of the sequence are converted to the desired display format (e.g., sector, linear, 3D, etc.) by a scan converter 50 which displays the graphically produced borders over the defined border locations in the ultrasound images. The image with its graphic border overlay are stored in a Cineloop memory 460. The images are then coupled to the video processor 470 for display.

Specific points on the identified borders of the successive images are tracked by the speckle tracker 142. which tracks the starting anatomical positions of the points by the speckle pattern produced by the local tissue at the image locations of the points. The speckle tracker 142 identifies regions of pixels around the reference points in the adjacent myocardium. The speckle patterns of these pixels are saved and compared with speckle patterns in the same regions of the successive images and the speckle patterns matched by block matching, as described in U.S. Pat. No. 6,442,289 (Olsson et al.) The difficulty and precision of the matching is determined by establishing a maximum correlation for the matching. The reference point locations in the images are thus tracked from image to image by following the speckle patterns around the points. When the speckle tracker 142 locates the reference points in a new image the reference point locations are coupled to the graphics processor 148, the border redrawn using the newly identified point locations, and a graphic overlay produced for the new image. The new image and its graphic overlay are scan converted and displayed on image display 480.

Speckle tracking is preferred over extraction of image gradients at the myocardial border by reason of its lower sensitivity to noise in the image. In addition there is no well-defined gradient for the epicardial border which, unlike the endocardial border is not defined by an adjacent blood pool. Furthermore, image noise can cause dropouts in the delineated border, causing estimates of the border to appear deeper into the myocardium rather than at the tissue boundary. A fairly well defined speckle patter has been found to track with reasonable accuracy from frame to frame in the presence of noise. However it has been found that the speckle pattern will change over time. This tendency can be countered by seeding the speckle pattern location at multiple locations in the stored images of a heart cycle, then tracking backward and forward in time from the two defined borders to cause convergence of a drifting speckle pattern. The seeding is performed by delineating two borders at, for example, the beginning and ending of the heart cycle using the automated or semi-automated border detection techniques described below or by manually defining the border by hand. Once the endocardial border has been defined this border can be expanded uniformly outward in all directions, then manually adjusting the border to the epicardial border viewed in the image. The convergence technique has been found to perform well over frame sequences of 80-300 frames, with 30-100 frames contained within one heart cycle.

Instead of tracking the speckle pattern of the myocardial tissue surrounding, underlying, or adjacent to the reference points, it may be appreciated that the reference point locations may be tracked by means other than speckle tracking, that is, by tracking image characteristics which are greater than a wavelength in size. For instance, the movement of specific anatomical features may be tracked. As another example, tissue texture may be tracked. It will also be appreciated that the targeted characteristics may be tracked in either pre-scan converted or post-scan converted image data.

Figure 3A:
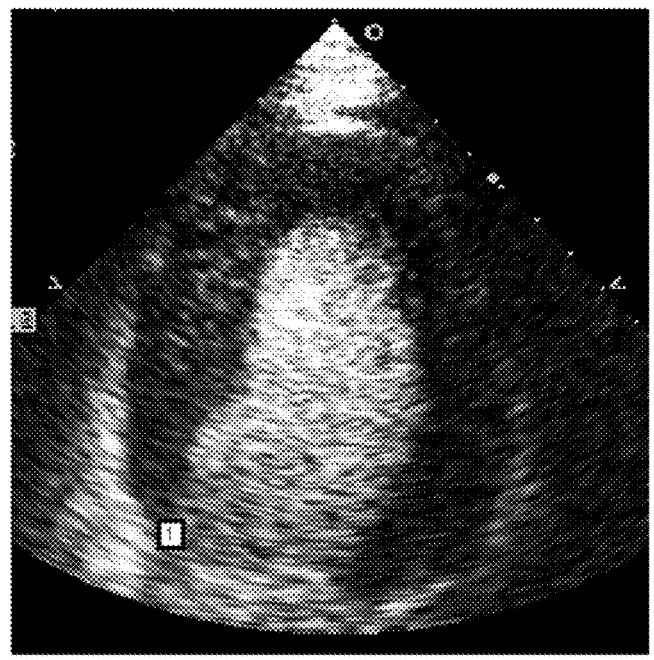
FIGS. 3a-3c illustrate a technique for detecting the endocardial border of the left ventricle in an ultrasound image.
Figure 3B:
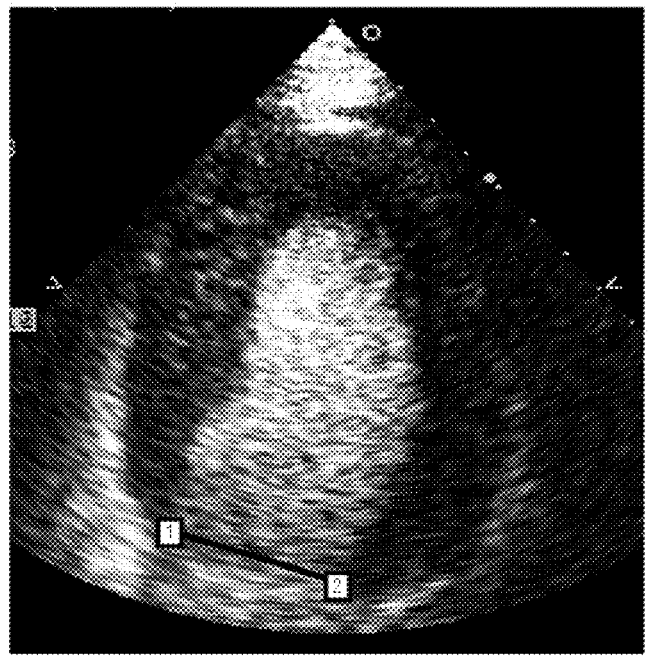
Figure 3C:
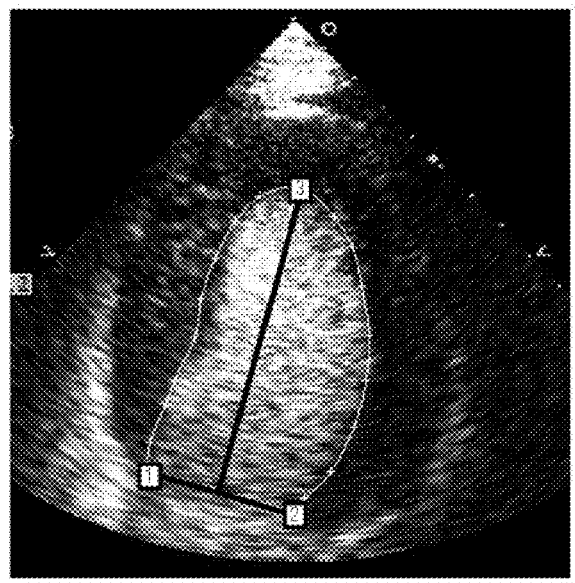

FIGS. 3a, 3b, and 3c illustrate contrast-enhanced long axis images of the left ventricle (LV) in which the border of the LV is traced. The user designates a first landmark in the image with a pointing device such as a mouse or a trackball, usually located on the ultrasound system control panel 150 or with a workstation keyboard, which manipulates a cursor over the image. In the example of FIG. 3a, the first landmark designated is the medial (septal) mitral annulus (MMA). When the user clicks on the MMA in the image, a graphic marker appears such as the white control point indicated by the number "1" in the drawing. The user then designates a second landmark, in this example the lateral mitral annulus (LMA), which is marked with the second white control point indicated by the number "2" in FIG. 3b. A line produced by the ABD processor then automatically connects the two control points, which in the case of this long axis view of the left ventricle indicates the mitral valve plane. The user then moves the pointer to the endocardial apex, which is the uppermost point within the left ventricular cavity. As the user moves the pointer to this third landmark in the image, a template shape of the left ventricular endocardial cavity dynamically follows the cursor, distorting and stretching as the pointer seeks the apex of the LV chamber. This template, shown as a white line in FIG. 3c, is anchored by the first and second control points 1 and 2 and passes through the third control point "3", which is positioned at the apex when the user clicks the pointer at the apex. When positioned, the endocardial cavity template provides an approximate tracing of the endocardium as shown in FIG. 3c. In the embodiment of FIG. 3c a black line which bisects the left ventricle follows the pointer as it approaches and designates the apex. This black line is anchored between the center of the line indicating the mitral valve plane and the left ventricular apex, essentially indicating a center line between the center of the mitral valve and the apex of the cavity. In commercial implementations the ABD processor 144 is available onboard ultrasound systems or in offline workstation form from Philips Medical Systems of Andover, Mass. in an image analysis package known as "QLAB™." This feature of the QLAB package is more fully described in US patent publication 2005/0075567 (Skyba et al.) The automated border processing can be fully automated by other means, such as that described in U.S. Pat. No. 6,491,636 (Chenal et al.)

Figure 4:
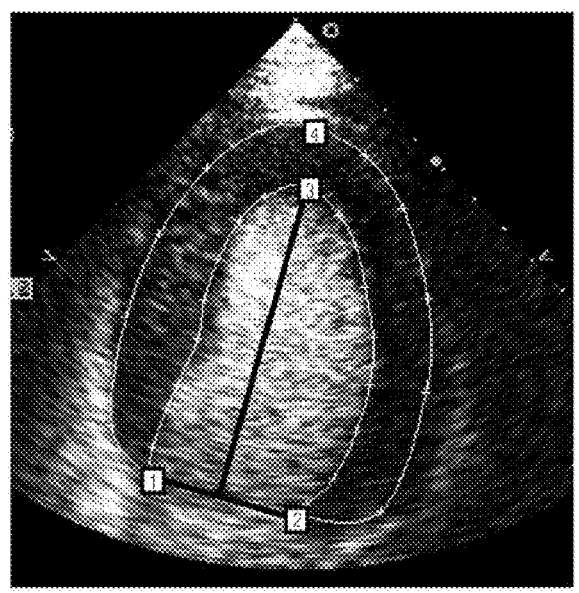
FIG. 4 illustrates an extension of the technique of FIGS. 3a-3c for detection of the epicardial border of the left ventricle in an ultrasound image.

In accordance with a further aspect of the present invention the ABD processor 144 is also capable of tracing the epicardial border of the myocardium as shown in FIG. 4. The epicardial border tracing can be done in a continuous process starting with the endocardial identification steps illustrated in FIGS. 3a, 3b, and 3c. With the endocardial border thus defined, the user moves the cursor to the epicardial apex, the uppermost point on the outer surface of the myocardium. The user then clicks on the epicardial apex and a fourth control point marked "4" is positioned. A second trace then automatically appears which approximately delineates the epicardial border as shown in FIG. 4. This second trace, shown by the outer white border line in FIG. 4, is also anchored by the first and second control points and passes through the positioned fourth control point at the epicardial apex. The two traces are an approximate outline of the myocardial border.

As a final step, the user may want to adjust the traces shown in FIG. 4 so that they precisely outline the border of the myocardium. Located around each tracing are a number of small control points shown in the drawing as "+" symbols. The number and spacing of these small control points is a system design choice or may be a variable that the user can set. Using a control on the user interface or control panel 150, the user can point at or near these control points and click and drag the outline to more precisely delineate the myocardial boundary in the image. This process of stretching or dragging the border is known as "rubberbanding", and is described more fully in the aforementioned U.S. Pat. No. 6,491,636, with particular reference to FIG. 9 of that patent. As an alternative to rubberband adjustment, in a more complex embodiment the approximated borders may automatically adjust to the image borders by image processing which uses the intensity information of the pixels at and around the approximated tissue borders. When finished, the border can precisely delineate the boundary of the myocardium by enclosing the image pixels of the myocardium in the image.

Figure 5:
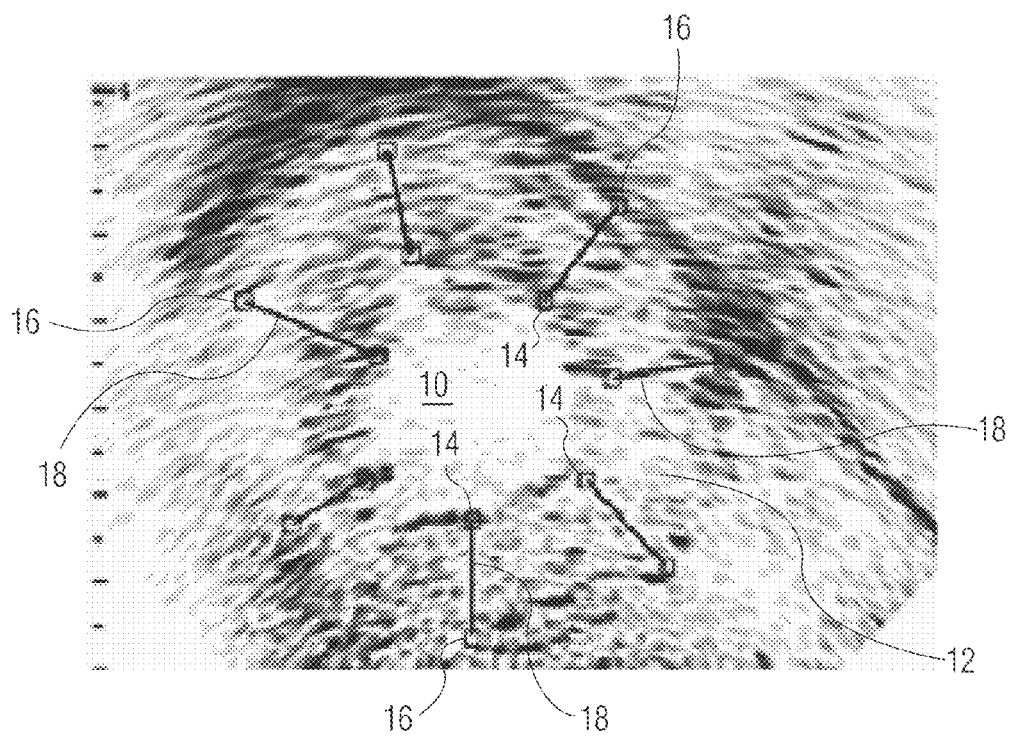
FIG. 5 illustrates an ultrasound image with graphics used to measure wall thickening in accordance with the principles of the present invention.

FIG. 5 illustrates a short axis cardiac image produced by an ultrasound system constructed in accordance with the principles of the present invention. The heart chamber 10 is shown in the center of the short axis image, surrounded by the myocardium 12. The endocardial and epicardial borders are defined using the techniques described above or those described in U.S. Pat. No. 5,797,396 (Geiser et al.), for instance. A number of reference points are defined on both the endo- and epi-cardial borders. Each pair of endo- and epi-cardial reference points 14,16 in this example comprises two points positioned at a separate radius of the short axis view. Each pair of reference points is joined by a graphically drawn chord line 18 produced by the graphics processor 148 which connects the points and is orthogonal to the borders in the initial image. In this example the border tracing graphics are not displayed; only the endo- and epi-cardial reference points 14,16 and their connecting chords 18 are displayed. In this example the reference points for seven lines are positioned around the myocardium and seven chord lines are drawn, although in a given implementation a greater or lesser number of chords can be used or user-defined by means of the user interface 150. As the reference point locations are modified by the user their values in the reference point data file 146 are correspondingly updated. The chord lines can be continuous between the associated reference points or can be segmented between the points for more detailed analysis of the line segment variations.

As the sequence of images moves from frame to frame through the cardiac cycle, the endo- and epi-cardial borders will change from image to image as the heart muscle contracts during systole, then relaxes during diastole. The reference points 14,16 continue to track the same positions on the respective borders due to the speckle tracking of their locations. As the heart muscle contracts to eject blood from the chamber, the endocardium should relatively uniformly move toward the center of the chamber and the lengths of the chords 18 should lengthen: the endo- to epi-cardial thickness increases. The variation in the lengths of the wall thickness chords can then be compared as shown by the seven corresponding transmural wall thickening curves 30 in FIG. 6, which are produced by the wall thickening curve calculator 20. In this example the wall thickening curves 30 are plotted against an acoustic quantification curve 32-38 which shows the changing heart chamber volume. The acoustic quantification (AQ) curve may be produced as described in U.S. Pat. No. 5,195,521 (Melton Jr. et al.) During the initial portion 32 of the AQ curve this heart chamber is ejecting blood until a point 34 of minimum chamber volume is reached. During this time the heart wall should be thickening until a point of maximum thickness 40 is attained. In this example all of the wall thickening curves attain a maximum at approximately the same time 40, characteristic of a healthy heart. If a heart is diseased such as occurs with an infarction, the chord at the infarcted location may not attain its maximum thickness at the same time as the healthy locations or will attain a lesser maximum thickness as the infarcted region is dragged along by the neighboring healthy regions, as shown by wall thickness curve 42.

From the point 34 of maximum contraction the heart muscle of the LV will begin to relax during portion 36 of the AQ curve as the heart refills with blood from the lungs, and the wall thickness will decrease as shown by the decreasing curves 30 during this time. The relaxed heart will plateau during the latter portion of diastole until a final atrial "kick" 38 is experienced when the left atrium contracts.

It is not strictly necessary for the chord reference points to be located exactly on the epi- and endo-cardial borders. An ROI can be defined by a user selected number of reference points 14 located some distance into the myocardium from the endocardial border (the ROI endocardium). Corresponding points are defined a further user-selected distance into the myocardium (the ROI epicardium). The ROI points are freehand refined if desired so that its endo- and epicardial points match the perceived tissue regions. Locating the point some distance into the tissue rather than exactly on the border will better assure their placement in a speckle pattern susceptible to tracking over the subsequent frames of the cardiac cycle. The ROIs need rely only on definition for a single frame at the beginning of the cardiac cycle and are subsequently re-defined by the updates from the tracking.

Figure 6:
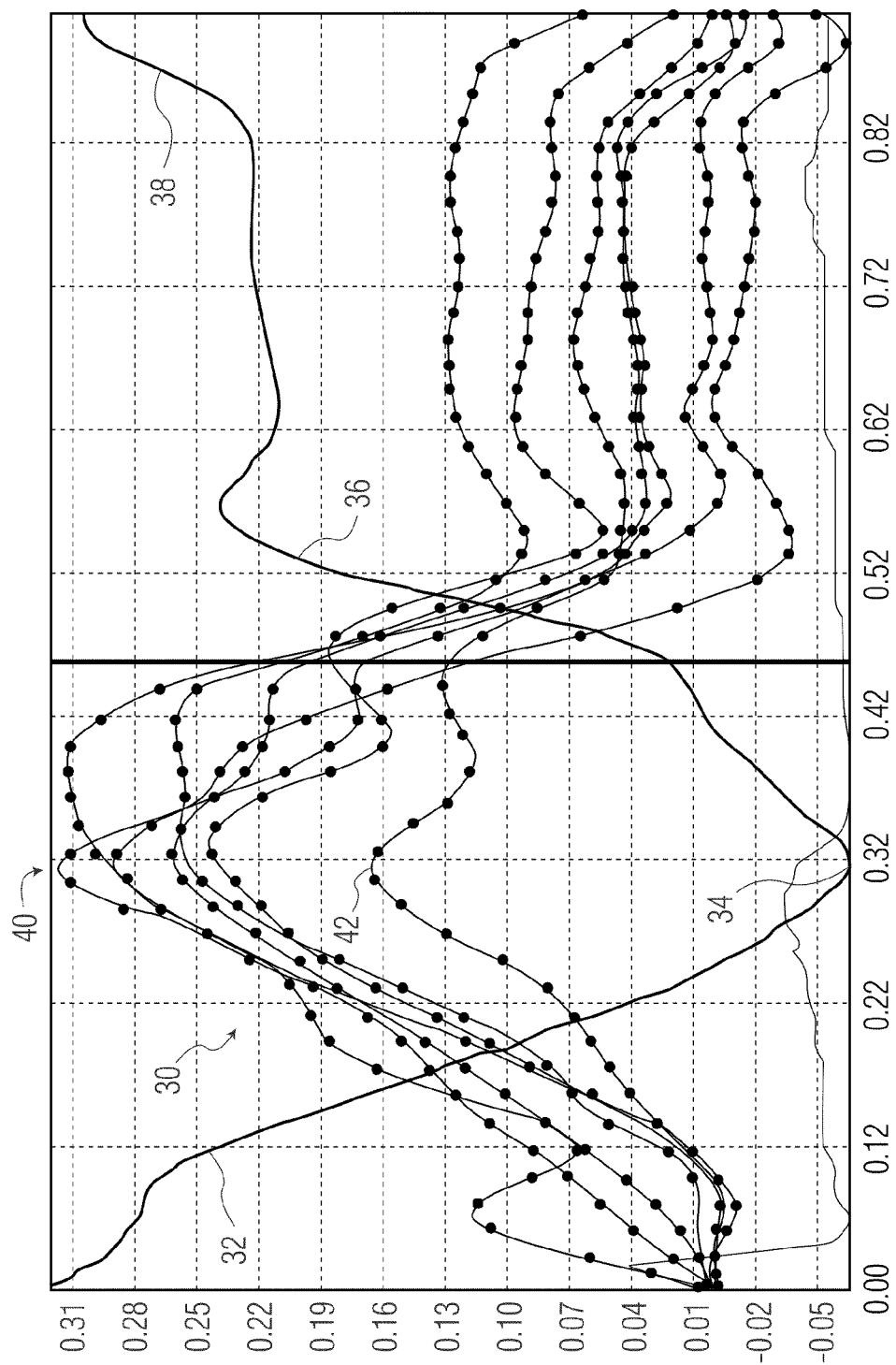
FIG. 6 illustrates a graphical plot of wall thickness measurements over a heart cycle in accordance with a further embodiment of the present invention.

Alternatively or in addition to tracking the chord length variation as shown in FIG. 6, the Lagrangian strain (fractional change in length relative to initial length) may be calculated by the wall thickening curve calculator 20 and graphically displayed. Strain is a measure of deformation in tissue and is an indicator of the mechanical effects of muscle tissue. See, for instance, U.S. Pat. No. 6,537,221 (Criton et al.) In accordance with a further aspect of the present invention the accumulated strain from the endocardium to the epicardium may be displayed and analyzed. The length and strain calculations for each endo- and epicardial pair of reference points 14,16 in the ROIs are displayed in graphs versus time with reference graphs of ventricular area, ejection fraction, or the ECG displayed for comparison, as shown in the graph of FIG. 6. In other implementations the length and strain variations may be displayed in a parametric image in colors or graphical representations over the tissue image of FIG. 5, enabling the clinician to readily identify abnormal variations in relation to their positions in the myocardial tissue.

What is claimed is:
1. An ultrasonic diagnostic imaging system for diagnosing heart wall thickening comprising:
a probe which acts to transmit ultrasonic waves into a heart and receives echoes in response;
an image processor responsive to the echoes which operates to produce a sequence of image frames of the myocardium over at least a portion of a cardiac cycle;

a myocardial wall thickness delineator which delineates distance between the endocardium and epicardium of the myocardium in each of the image frames of the sequence by use of an image tracker which acts to track the delineated distance from frame to frame through the portion of the cardiac cycle; and a wall thickness analyzer, responsive to the delineated distances, which operates to produce a graphical wall thickening curve of the continuous variation in myocardial wall thickness over the portion of the cardiac cycle.

2. The ultrasonic diagnostic imaging system of claim 1, wherein the image tracker further comprises a speckle tracker.

3. The ultrasonic diagnostic imaging system of claim 1, wherein the image tracker further comprises an anatomical feature tracker.

4. The ultrasonic diagnostic imaging system of claim 1, wherein the image tracker further comprises a texture tracker.

5. The ultrasonic diagnostic imaging system of claim 1, wherein the wall thickness analyzer further operates to produce a graphical wall thickening curve of the variation of the lengths of chords directed across the myocardium.

6. The ultrasonic diagnostic imaging system of claim 5, wherein the wall thickness analyzer further operates to produce an indication of the variation of the distance between the endocardium and the epicardium.

7. The ultrasonic diagnostic imaging system of claim 1, further comprising:

an anatomical border detector, responsive to images of the myocardium, which operates to delineate the endocardial and epicardial borders of the myocardium, wherein the wall thickness analyzer operates to produce a graphical wall thickening curve of variation between the endocardial and epicardial borders.

8. The ultrasonic diagnostic imaging system of claim 7, wherein the wall thickness analyzer further operates to produce wall thickening curves indicating variation between the endocardial and epicardial borders at selected locations around the heart chamber.

9. The ultrasonic diagnostic imaging system of claim 8, wherein the wall thickness analyzer further operates to produce a quantified measure of variation between the endocardial and epicardial borders at selected locations around the heart chamber over at least a portion of a cardiac cycle.

10. The ultrasonic diagnostic imaging system of claim 9, wherein the quantified measure comprises a graphical display.

11. The ultrasonic diagnostic imaging system of claim 1, wherein the wall thickness analyzer operates to produce an indication of strain across at least a portion of the myocardium.

12. The ultrasonic diagnostic imaging system of claim 11, wherein the wall thickness analyzer operates to produce an indication of Lagrangian strain across at least a portion of the myocardium.

13. The ultrasonic diagnostic imaging system of claim 12, wherein the wall thickness analyzer operates to produce a quantified measure of Lagrangian strain across at least a portion of the myocardium over at least a portion of a cardiac cycle.

14. The ultrasonic diagnostic imaging system of claim 13, wherein the quantified measure comprises a graphical display.

* * * * *